United States Patent [19]

Ahrgren et al.

[11] Patent Number: 4,591,638
[45] Date of Patent: May 27, 1986

[54] DEXTRAN OR CROSSLINKED DEXTRAN HAVING QUATERNARY AMINO GROUPS

[75] Inventors: Leif G. Ahrgren, Tierp; Anthony N. de Belder, Upsala, both of Sweden

[73] Assignee: Pharmacia AB, Upsala, Sweden

[21] Appl. No.: 377,193

[22] Filed: May 11, 1982

[30] Foreign Application Priority Data

May 19, 1981 [SE] Sweden ................................ 8103137

[51] Int. Cl.$^4$ ................................................. C08B 37/02
[52] U.S. Cl. ............................................ 536/51; 536/112
[58] Field of Search ............................... 536/112, 51

[56] References Cited

U.S. PATENT DOCUMENTS

| | | | |
|---|---|---|---|
| 2,989,409 | 6/1961 | Hiler | 536/51 |
| 3,042,667 | 7/1962 | Flodin et al. | 536/112 |
| 3,277,025 | 10/1966 | Flodin et al. | 536/51 |
| 3,629,230 | 12/1971 | Folke | 536/51 |
| 3,652,540 | 3/1972 | Determann et al. | 536/51 |
| 3,865,807 | 2/1975 | Narang et al. | 536/51 |
| 4,189,534 | 2/1980 | Levine et al. | 435/2 |
| 4,293,654 | 10/1981 | Levine et al. | 536/51 |

FOREIGN PATENT DOCUMENTS 2484419  6/1981  France .

Primary Examiner—Johnnie R. Brown
Assistant Examiner—Elli Peselev
Attorney, Agent, or Firm—Fred Philpitt

[57] ABSTRACT

The invention relates to a new polymer containing quarternary amino group based on dextran or crosslinked dextran. The quarternary amino groups are of the formula

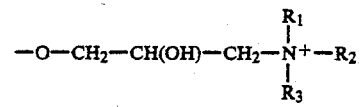

where $R_1$, $R_2$ and $R_3$, which may be identical or different, are lower alkyl groups of 1–5 carbon atoms or lower hydroxyalkyl groups of 2–5 carbon atoms and 1–2 hydroxy groups. At most one atom other than carbon and hydrogen is bound to the same carbon atom in the hydroxy alkyl group.

15 Claims, No Drawings

DEXTRAN OR CROSSLINKED DEXTRAN HAVING QUATERNARY AMINO GROUPS

The present invention relates to new polymers containing quarternary amino groups and being based on dextran or cross-linked dextran, which polymers do not split off toxic substances.

For a long time it has been known that polymers containing diethylaminoethyl groups and being based on cross-linked dextran have been used as ion exchangers and as therapeutical agents e.g. as an agent for binding bile acids in the treatment of hypercholesterolemia. Corresponding non-cross-linked products have also been used as therapeutical agents. For such products, however, it has been found that there exists a risk for leakage of toxic substances from the product. The reason for the instability observed is that, during the substitution with diethylaminoethyl groups, a number of so called "tandem groups" are formed.

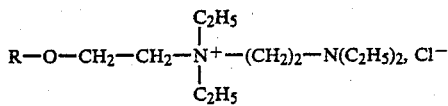

where R is the dextran matrix, which may be cross-linked. As described by Ahrgren et al (Polymeric Amines and Ammonium Salts, Editor Goethals, Pergamon Press, Oxford and New York, 1980) these tandem groups are able to degrade under formation of diethylaminoethyl chloride (DEAE-Cl). The reaction which passes through the intermediary aziridinium ion, also gives diethylaminoethyl alcohol and piperazinium ion. At storage tests at 30° C. a content of free DEAE-Cl of about 30 ppm was found after 15 days. The risk for leakage of this toxic substance makes diethylaminoethyl substituted polymers less suitable for therapeutical purposes and ion exchange purposes, as products which have been separated might have been contaminated with such toxic substances.

According to the present invention it has been found that it is possible to synthesize polymers containing quarternary amino groups, which do not have the drawbacks previously mentioned. Thus, the invention relates to a polymer having quarternary amino groups and being based on dextran or cross-linked dextran and which polymer is characterized in that the quarternary amino groups have the formula:

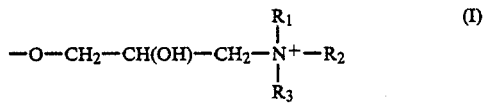

where $R_1$, $R_2$ and $R_3$, which may be identical or different, are lower alkyl groups of 1-5 carbon atoms or lower hydroxyalkyl groups of 2-5 carbon atoms and 1-2 hydroxy groups, at most one atom other than carbon and hydrogen being bound to the same carbon atom of the hydroxyalkyl group. —O— in the group (I) originates from the polymeric base skeleton. Thus, the substituent (I) is bound by ether bonds to the base polymer.

$R_1$, $R_2$ and $R_3$ may for instance be lower alkyl groups of 1 or 2 carbon atoms, $R_1$, $R_2$ and $R_3$ may for instance be methyl. As an example of a lower hydroxyalkyl group 2-hydroxyethyl and 2-hydroxypropyl may be mentioned.

Counter ions to the aforementioned quarternary amino groups may be inorganic or organic negative ions, eg chloride ions, nitrate ions or sulfate ions or negative ions of different organic acids. Non-toxic counter ions are of course selected, when the product so requires.

When insoluble polymers are required, the dextran is suitably cross-linked to a three-dimensional network, which is insoluble but swellable in water.

Such cross-linking bridges are preferred, which are bound to the dextran chains by ether bonds. However, other bonds may also be selected, when the demand for stability against hydrolysis is lower. Thus, the bridges may also eg be bound to the dextran chains by ester bonds. Ester bound bridges are eg obtained by reacting dextran or a dextran derivative with reactive derivatives of dicarboxylic acids eg diacyl halides.

Preferably the cross-linking bridges, which are bound via ether bridges, comprise straight or branched, aliphatic, saturated hydrocarbon chains being substituted with one or more (preferably 1-3) hydroxyl groups and containing 3-20 carbon atoms (preferably 3-10 carbon atoms) and being possibly broken by one or more (preferably 1-3) oxygen atoms. It is suitable that at most one oxygen atom is bound to the same carbon atom in the bridge.

The dextran or the cross-linked dextran may also be substituted with groups other than those substituents comprising the quarternary amino groups or the cross-linking substituents, when such ones are present. Examples of such other substituents are hydroxyalkyl groups, eg of 2-5 carbon atoms, as 2-hydroxypropyl and 2-hydroxybutyl, which groups may give cross-linked dextran properties of swelling in water as well as in certain organic solvents, eg mixtures of water and ethanol. Another example of such substituents is 2,3-dihydroxypropyl.

Depending on use, the substitution degree of the quarternary amino groups may be varied large ranges. The mean substitution degree may eg be in the range of 0.05 to 3, such as 0.1 to 2 substituents per anhydroglucose unit of the dextran. The degree of substitution of the insoluble cross-linked dextran products may be such that the ion exchange capacity for instance is in the range of 0.1-6, such as 0.2-5 meq/g (calculated per gram of dry product with chloride as counter ion).

The insoluble products according to the invention are swellable in water and the swelling degree may be varied within wide ranges. For instance each gram of the product may adsorb 1 to 100 grams of water, eg 2 to 20 grams of water, as 3 to 15 grams of water. Like the previously known ion exchangers, they may be prepared in the form of particles by grinding of larger particles. It is also possible to synthesize spherical particles by so-called bead-polymerisation.

In the cross-linked product the total substitution degree of the quarternary amino groups and of the substituents originating from the cross-linking agent may be varied within wide ranges. The mean total substitution degree may eg be in the range of 0.2 to 3, such as 0.6 to 2.5 for instance 0.7 to 2 substituents per anhydroglucose unit.

The products according to the invention are preferably synthesized by reacting, in an alkaline aqueous solution preferably a solution of an alkalihydroxide, a soluble dextran or an insoluble and cross-linked dextran with a quarternary ammonium ion of the structure

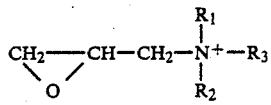

or corresponding halohydrins, where $R_1$, $R_2$ and $R_3$ have the meanings given above.

One alternative method is to react the soluble or insoluble dextran with epihalohydrin or corresponding dihalohydrin for introducing reactive oxirane or halohydrin groups. These reactive groups may then be reacted with tertiary amines having the structure

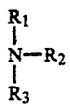

where $R_1$, $R_2$ and $R_3$ have the meanings given above.

The cross-linking may be carried out in a way known per se by the use of a bifunctional cross-linking agent. Examples of cross-linking agents are epichlorohydrin and 1,4-butanediol diglycidyl ether. Preferably the cross-linking is carried out before the substitution. Purification between the two different steps is not necessary, but may of course be carried out if it is required.

The invention also relates to pharmaceutical compositions, which are characterized in that they comprise a therapeutical effective dose of the product according to the invention. Of course, in this case a non-toxic negative ion is selected as counter ion to the quarternary amino group. The invention also relates to a method of treating patients having raised blood levels of cholesterol, which method is characterized by oral administration of a therapeutically effective dose of such a pharmaceutical composition to the patients.

The invention will now be illustrated by the following working examples, which do not limit the invention.

EXAMPLE 1

Dextran ($\bar{M}_w = 10\,000$): 15 kg
Dist. water: totally 19.2 l
NaOH: 3 kg
NaBH$_4$: 75 kg
Toluene: totally 55 l
Emulgator (GAFAC$^R$ PE 510, from General Aniline Film Corp, USA): 0.9 kg
Epichlorohydrin: 5.6 l
G-MAC$^R$ (Glycidyl trimethyl ammonium chloride from Shell International Chem Co): 30 kg Dextran was dissolved in water (15.6 l) in a vessel of 50 l. NaOH and NaBH$_4$ were dissolved in water (3.6 l) and mixed with the dextran solution in a stainless boiler (140 l) and stirred for 24 hours at 50° C. Toluene and emulgator were added and the mixture was conditioned over night, in order to get rid of gas bubbles originating from NaBH$_4$. The mixture was stirred for 1 hour at 600 r.p.m. Epichlorohydrin was added and after 3.3 hours the emulsion was transferred to a boiler of 250 l. After 0.2 hours 7.5 kg G-MAC$^R$ was added while stirring at 50° C. and after another 30 minutes 7.5 kg more of G-MAC$^R$ was added. The mixture became very viscous and remained so for 30 more minutes when 10 l toluene was added followed by a new 7.5 kg portion of G-MAC$^R$. After another 30 minutes a new 7.5 kg portion of G-MAC$^R$ were added whereafter the reaction was left over night at 50° C.

The next day 100 l ethanol was added and after stirring for 30 minutes the mixture was allowed to sediment. Thereafter the gel particles were washed 7 times with ethanol (150 l), 5 times with diluted hydrochloric acid (250 l, pH 3) and finally 4 times with ethanol (250 l). The product was filtered off and dried for 72 hours at 50° C.

The yield was 32 kg. The capacity was 3.4 meq/g of the dry product with chloride as counter ion.

EXAMPLE 2

Dextran ($\bar{M}_w = 10\,000$): 150 g
Dist. water: 222 ml
Toluene: 150 ml
Emulgator (GAFAC$^R$ PE 510): 45 g
NaOH: 7.5 g
OGTAC$^R$ (85%) (G-MAC$^R$, 85%, aqueous solution): 150 g
NaBH$_4$: 0.9 g
G-MAC$^R$ (100%): 150 g
Calofort$^R$ S (Calcium carbonate coated with calcium stearate, Sturge Chemicals, England): 45 g
1,4-Butanediol diglycidyl ether: 200 g Dextran was dissolved in 180 ml water, OGTAC$^R$ was added and 2.5 g NaOH and NaBH$_4$ in 44 ml water. The mixture was stirred for 4 hours at room temperature. 10 g NaOH was dissolved in the dextran solution. Toluene, emulgator and Calofort were mixed and the temperature adjusted to 70° C. The mixture was then added to the dextran solution. The resulting reaction mixture was stirred at 1,400 rpm for 1 hour. The temperature was allowed to drop to 50° C. and 1,4-butanediol diglycidyl ether was added. The reaction was allowed to continue with stirring over night.

The product was poured into 500 ml ethanol, stirred for 10 minutes and was finally allowed to sediment. Washing was repeated three times with ethanol, twice with diluted HCl (pH 3) and finally three times with ethanol (99.5%).

The yield was 53 g. The capacity was 2.4 meq/g of the dry product with chloride as counter ion.

EXAMPLE 3

Storage stability

The product from example 1 was kept at 30° C. in a glass vessel and was analysed after 1 and 3 months respectively. 15 g substance was extracted by 150 ml water for 1 night, whereafter the amount of alkylating compounds was determined by use of nitrobensyl reagents (J Epstein et al; Anal Chem 27, 1955 p 1435) and the amount of carbohydrates by the anthrone method (J Burt; Anal Biochem 9, 1964, p 293).

When analysing the extract the following values were obtained.

|  | 1 month | 3 months |
| --- | --- | --- |
| pH | 5.2 | 4.9 |
| Extractable substances (mg/g) | 1.4 | 1.5 |
| Carbohydrates (mg/g) | 0.09 | 0.25 |
| Alkylating substances (ppm) | >1 | >1 |
| Trimethyl amine (mg/g) | 0.033 | 0.033 | pH was determined in a mixture of 0.5 g product in 30 ml 1 M KCl.

Of special importance is the observation that no alkylating substances are formed during storage.

EXAMPLE 4

Cholesterol lowering effect

Five weeks old cockerels (about 1 kg each) were divided into four groups of 10 animals each. All the cockerels were fed during the trial with a base diet consisting of Pullfor$^R$ Startfoder (AB Fors, Sweden). After five days group II was given 2% cholesterol and 1% DEAD Sephadex$^R$ (Pharmacia Fine Chemicals AB, Uppsala, Sweden) in their base diet, while group III was given 2% cholesterol and 1% of the product from example 1 in their base diet.

The reference group was group I, which during the entire experiment was kept on the pure base diet and group IV was given 2% cholesterol in their base diet.

After nine days (including the five starting days on pure base diet) the feeding was interrupted and the animals fasted on 18 hours and blood samples were collected by heart puncture.

| Results Group | Serum cholesterol (mg/100 ml) |
|---|---|
| I | 138 ± 6 |
| II | 142 ± 5 |
| III | 148 ± 13 |
| IV | 240 ± 25 |

Thus the product from example 1 gives a significant lowering of the serum content of cholesterol. This lowering is of the same size as for DEAE Sephadex$^R$.

We claim:

1. A polymer consisting of dextran or crosslinked dextran containing quarternary amino groups wherein the quarternary amino groups have the formula

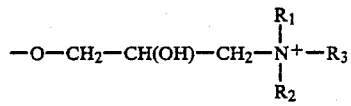   (I)

where $R_1$, $R_2$ and $R_3$, which may be identical or different, are lower alkyl groups of 1–5 carbon atoms, or lower hydroxyalkyl groups having 2–5 carbon atoms and 1–2 hydroxy groups with at most one hydroxy group being bound to one and the same carbon atom in the hydroxyalkyl group.

2. A polymer according to claim 1 wherein each of $R_1$, $R_2$ and $R_3$ is a lower alkyl group of 1–2 carbon atoms.

3. A polymer according to claim 1 or 2 wherein the dextran is crosslinked to a three-dimensional network and is insoluble but swellable in water.

4. A polymer according to claim 1 wherein $R_1$, $R_2$ and $R_3$ are methyl.

5. A polymer according to claim 1 wherein at least one of the groups $R_1$, $R_2$ and $R_3$ is selected from the group of 2-hydroxyethyl, 2-hydroxypropyl and 2,3 dihydroxy propyl.

6. A polymer according to claim 1 wherein the dextran is cross-linked by bridges, which are bound to the dextran chains by ether bonds, said bridges comprising straight or branched, aliphatic, saturated hydrocarbon chains being substituted with one or more hydroxyl groups, and containing 3–20 carbon atoms, and being broken by one or more oxygen atoms, no more than one oxygen atom being bound to one and the same carbon atom in the bridge.

7. A polymer according to any one of claims 1, 2, 4, 5 or 6 wherein the means degree of substitution of the quaternary amino groups in the dextran or cross-linked dextran is within the range of 0.05–3.

8. A polymer according to claim 7 wherein the dextran is crosslinked to a degree that it is insoluble in water and each gram can absorb 2 to 20 grams of water.

9. A polymer according to claim 3 wherein the ion exchange capacity is in the range of 0.1–6 meq/g calculated per gram of dry product with chloride as counter ion.

10. An insoluble ion-exchanger, substantially free from leakage of toxic compounds, consisting of crosslinked dextran containing quarternary amino groups wherein the quarternary amino groups have the formula

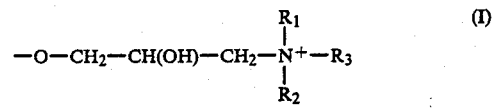   (I)

wherein $R_1$, $R_2$ and $R_3$, which may be identical or different, are lower alkyl groups of 1–5 carbon atoms, or lower hydroxyalkyl groups having 2–5 carbon atoms and 1–2 hydroxy groups with at most one hydroxy group being bound to one and the same carbon atom in the hydroxyalkyl group.

11. An ion-exchanger according to claim 10 wherein each of $R_1$, $R_2$ and $R_3$ is a lower alkyl group of 1–2 carbon atoms.

12. An ion-exchanger according to claim 10 wherein at least one of the groups $R_1$, $R_2$ and $R_3$ is selected from the group of 2-hydroxyethyl, 2-hydroxypropyl and 2,3 dihydroxy propyl.

13. An ion-exchanger according to claim 10 wherein the dextran is cross-linked by bridges, which are bound to the dextran chains by either bonds, said bridges comprising straight or branched, aliphatic, saturated hydrocarbon chains being substituted with one or more hydroxyl groups, and containing 3–20 carbon atoms, and being broken by one or more oxygen atoms, no more than one oxygen atom being bound to one and the same carbon atom in the bridge.

14. An ion-exchanger according to claim 10 wherein the mean degree of substitution of the quaternary amino groups in the dextran or cross-linked dextran is within the range of 0.05–3.

15. An ion-exchanger according to claim 10 wherein the ion exchange capacity is in the range of 0.1–6 meq/g calculated per gram of dry product with chloride as counter ion.

* * * * *